US009067011B2

(12) United States Patent
Zou et al.

(10) Patent No.: US 9,067,011 B2
(45) Date of Patent: Jun. 30, 2015

(54) DEVICE FOR DELIVERY OF POWDER LIKE MEDICATION IN A HUMID ENVIRONMENT

(75) Inventors: Hans Zou, Windsor, NJ (US); Jeff Shimizu, Cortlandt Manor, NY (US); Lucian R. Albu, Forest Hills, NY (US); Johan F. Dijksman, Weert (NL)

(73) Assignee: Medimetrics Personalized Drug Delivery B.V., Eindhoven (NL)

( * ) Notice: Subject to any disclaimer, the term of this patent is extended or adjusted under 35 U.S.C. 154(b) by 765 days.

(21) Appl. No.: 12/992,305

(22) PCT Filed: Jun. 17, 2009

(86) PCT No.: PCT/IB2009/052575
§ 371 (c)(1),
(2), (4) Date: Nov. 12, 2010

(87) PCT Pub. No.: WO2009/153739
PCT Pub. Date: Dec. 23, 2009

(65) Prior Publication Data
US 2011/0106064 A1    May 5, 2011

Related U.S. Application Data

(60) Provisional application No. 61/073,778, filed on Jun. 19, 2008.

(51) Int. Cl.
*A61K 9/22*   (2006.01)
*A61M 37/00*  (2006.01)
(Continued)

(52) U.S. Cl.
CPC ......... *A61M 5/14276* (2013.01); *A61M 31/002* (2013.01); *A61M 2202/064* (2013.01); *A61M 2205/3365* (2013.01); *A61M 2210/1053* (2013.01); *A61M 2210/1064* (2013.01)

(58) Field of Classification Search
USPC ................... 604/890.1, 891.1, 57–60, 82–84, 604/131–135, 151–155, 214, 218, 221–222, 604/228
See application file for complete search history.

(56) References Cited

U.S. PATENT DOCUMENTS 4,572,403 A   2/1986   Benaroya
4,814,180 A   3/1989   Eckenhoff et al.
(Continued)

FOREIGN PATENT DOCUMENTS

CN    1958090       5/2007
CN    100998905 A   7/2007
(Continued)

OTHER PUBLICATIONS

Chinese Office Action mailed Jan. 15, 2013 for Chinese patent application No. 201080015953.5, a counterpart foreign application of U.S. Appl. No. 13/262,841, 17 pages.
(Continued)

*Primary Examiner* — Andrew Gilbert
(74) *Attorney, Agent, or Firm* — Lee & Hayes, PLLC

(57) ABSTRACT

A device for placement in an environment, particularly a humid environment, for delivery of medication to said environment. The device comprises a reservoir (103) having an orifice (104), a conveying unit for conveying a reservoir's content (106) through the orifice (104) and an actuator arrangement for driving the conveying unit. In order to provide a reliable delivery of medication in a humid environment, the conveying unit comprises an auger (110) extending in the reservoir (103).

19 Claims, 3 Drawing Sheets

(51) Int. Cl.
*A61M 5/315* (2006.01)
*A61M 5/142* (2006.01)
*A61M 31/00* (2006.01)

(56) References Cited

U.S. PATENT DOCUMENTS

| | | | |
|---|---|---|---|
| 5,071,040 A * | 12/1991 | Laptewicz, Jr. | 222/235 |
| 5,279,607 A | 1/1994 | Schentag et al. | |
| 5,318,557 A * | 6/1994 | Gross | 604/891.1 |
| 5,423,779 A * | 6/1995 | Yeh | 604/317 |
| 5,567,592 A | 10/1996 | Benet et al. | |
| 6,053,899 A * | 4/2000 | Slanda et al. | 604/500 |
| 6,423,779 B2 * | 7/2002 | Sue et al. | 525/191 |
| 6,632,216 B2 * | 10/2003 | Houzego et al. | 604/890.1 |
| 6,699,214 B2 * | 3/2004 | Gellman | 604/82 |
| 6,803,373 B2 | 10/2004 | Schellens | |
| 6,929,636 B1 * | 8/2005 | von Alten | 604/890.1 |
| 7,014,640 B2 * | 3/2006 | Kemppainen et al. | 606/86 R |
| 7,030,132 B2 | 4/2006 | Schellens et al. | |
| 8,021,357 B2 * | 9/2011 | Tanaka et al. | 604/890.1 |
| 8,100,889 B2 * | 1/2012 | Kawano et al. | 604/891.1 |
| 8,308,681 B2 * | 11/2012 | Slocum et al. | 604/82 |
| 2002/0072735 A1 | 6/2002 | Kupperblatt et al. | |
| 2003/0020810 A1 | 1/2003 | Takizawa et al. | |
| 2003/0213495 A1 | 11/2003 | Fujita et al. | |
| 2004/0054278 A1 | 3/2004 | Kimchy et al. | |
| 2004/0242962 A1 | 12/2004 | Uchiyama | |
| 2005/0147559 A1 | 7/2005 | von Alten | |
| 2005/0234431 A1 * | 10/2005 | Williams et al. | 604/890.1 |
| 2006/0145876 A1 | 7/2006 | Kimura et al. | |
| 2006/0155174 A1 | 7/2006 | Glukhovsky et al. | |
| 2007/0138027 A1 | 6/2007 | Dinsmoor et al. | |
| 2007/0213659 A1 * | 9/2007 | Trovato et al. | 604/67 |
| 2007/0250045 A1 | 10/2007 | Trieu | |

FOREIGN PATENT DOCUMENTS

| | | |
|---|---|---|
| DE | 3317536 | 11/1984 |
| DE | 3317536 A1 * | 11/1984 |
| DE | 3339323 | 5/1985 |
| FR | 2794654 | 12/2000 |
| GB | 2374149 | 9/2002 |
| JP | 2002532162 | 10/2002 |
| JP | 2003520108 | 7/2003 |
| WO | WO9407562 | 4/1994 |
| WO | WO0152923 | 7/2001 |
| WO | WO03008637 | 1/2003 |
| WO | WO03068061 | 8/2003 |
| WO | WO2004066903 | 8/2004 |
| WO | WO2005025647 | 3/2005 |
| WO | WO2005038049 | 4/2005 |
| WO | WO2006021932 | 3/2006 |
| WO | WO2006025013 | 3/2006 |
| WO | WO2006037434 | 4/2006 |
| WO | WO2006044049 | 4/2006 |
| WO | WO2006056944 | 6/2006 |
| WO | WO2006077529 | 7/2006 |
| WO | WO2008029372 | 3/2008 |
| WO | WO2008038199 | 4/2008 |
| WO | WO2008062335 | 5/2008 |

OTHER PUBLICATIONS

Chinese Office Action mailed Jan. 21, 2013 for Chinese patent application No. 201080040663.6, a counterpart foreign application of U.S. Appl. No. 13/390,111, 8 pages.

Chinese Office Action mailed Mar. 14, 2013 for Chinese patent application No. 200980112018.8, a counterpart foreign application of U.S. Appl. No. 12/933,891, 12 pages.

Chinese Office Action mailed May 13, 2013 for Chinese patent application No. 201080015284.1, a counterpart foreign application of U.S. Appl. No. 13/262,861, 11 pages.

Evans, et al., "Measurement of Gastrointestinal pH Profiles in Normal Ambulant Human Subjects", GUT, vol. 29, 1988, pp. 1035-1041.

Japanese Office Action mailed Apr. 16, 2013 for Japanese Patent Applicaiton No. 2011-514179, a counterpart foreign application of U.S. Appl. No. 12/992,305, 9 pages.

Japanese Office Action mailed Apr. 30, 2013 for Japanese patent application No. 2010-546431, a counterpart foreign application of U.S. Appl. No. 12/867,888, 4 pages.

Kompella, et al., "Delivery System for Penetration Enhancement of Peptide and Protein Drugs: Design Considerations", Advanced Drug Delivery Reviews, vol. 46, 2001, pp. 211-245.

Paine, et al., "Characterization of Interintestinal and Intraintestinal Variations in Human CYP3A-Dependent Metabolism", The Journal of Pharmacology and Experimental Therapeutics, vol. 283, No. 3, 1997, pp. 1552-1562.

Siccardi, et al., "Regulation of Intestinal Epithelial Function: A Link Between Opportunities for Macromolecular Drug Delivery and Inflammatory Bowel Disease", Advanced Drug Delivery Reviews, vol. 57, 2005, pp. 219-235.

* cited by examiner

DEVICE FOR DELIVERY OF POWDER LIKE MEDICATION IN A HUMID ENVIRONMENT

CROSS REFERENCE TO RELATED CASES

Applicants claim the benefit of International Application Number PCT/IB2009/052575, filed Jun. 17, 2009, and Provisional Application Ser. No. 61/073,778, filed Jun. 19, 2008.

FIELD OF THE INVENTION

The invention relates to a device for placement in an environment for delivery of medication to said environment, comprising a reservoir having an orifice, a conveying unit for conveying a reservoir's content through the orifice and an actuator arrangement for driving the conveying unit. The invention further relates to a capsule provided with the device for placement in an environment to deliver medication to said environment.

BACKGROUND OF THE INVENTION

In WO 94/07562 delivery capsules are disclosed which include a beneficial agent and an activating mechanism, which delivery capsules are designed to deliver the beneficial agent in a pulsatile manner through the orifice. The pulsatile delivery is achieved by a pair of guide members inside the capsule, one secured to the capsule itself and the other to a movable partition.

Techniques disclosed in WO 94/07562 have limited ability to deliver a powder like medication in a humid environment to said environment since the techniques have no facility to annul a solidification of the powder like medication induced by humidification.

OBJECT OF THE INVENTION

It is an object of the invention to provide a device for a more reliable delivery of a medication in a humid environment.

SUMMARY OF THE INVENTION

The object of the invention is achieved by the device according to the invention which is characterized in that the conveying unit comprises an auger extending in the reservoir. By extending the auger in the reservoir, mechanical interaction with the reservoir's content is arrived at. As a result of the presence of at least a portion of the auger in the reservoir, in addition to conveying the powder like medication to the orifice of the reservoir, a solidification of a powder like medication contained in the reservoir through humidification in a moist environment or by way of a humidity already contained in the powder, is annulled through pulverization. Here, solidification of the powder like medication ranges from a wet paste to a solid. It is noted that the actuator arrangement can include one or more actuators known per se, such as a spring actuator, an electromagnetic actuator, a hydraulic actuator or a piezoelectric actuator. The auger can be made from a biocompatible plastic or a stainless steel.

In a preferred embodiment according to the invention, the conveying unit comprises a piston for pressurizing the reservoir's content. With that, under the pressure provided by the piston, the reservoir's content is continuously fed into an auger's helical flighting. As a result, a revolution of the auger eventuates at a well defined amount of powder like medication conveyed through the orifice.

In a further embodiment according to the invention, the conveying unit is provided with a facility for pretensioning the piston to the reservoir's content. As a result, a continuous energizing of the actuator arrangement for pressurizing the reservoir's content is not needed.

In a further embodiment according to the invention, the piston is driveable by the auger. As a result, the prerequisite for a further actuator to drive the piston is circumvented.

In an embodiment according to the invention a surface profile of the piston matches a profile of a reservoir's surface adjacent to or surrounding the orifice. As a result the residual reservoir's content is minimized. With that the yield of a capsule provided with this embodiment according to the invention is maximized.

In a further embodiment according to the invention, the conveying unit comprises a collapsible barrier for pressurizing the reservoir's content. The collapsible barrier is conformable to a curved surface of revolution enveloping the auger. By selecting the dimensions of the curved surface of revolution enveloping the auger to be sufficiently small, a residual reservoir's content is minimized. With that a yield of a capsule provided with this embodiment according to the invention is maximized.

In a further embodiment according to the invention, the auger has an axially varying helical flighting height. Herein the helical flighting height is defined as a radius measured from an auger's axis of revolution to a curved surface of revolution enveloping the auger.

In an embodiment according to the invention, the axially varying helical flighting height increases with an axial distance measured from the orifice. As a result, an axially oriented pressure gradient can be exerted by the auger on the reservoir's content contained within a volume established by a revolution of the auger. The helical flighting height preferably monotonically increases with the distance from the orifice. Proximal to the orifice, the helical flighting height matches a size of the orifice with the purpose of continuation of the auger up to and including the reservoir's orifice.

In an embodiment according to the invention the auger has an axially varying helical flighting pitch. In this text, the helical flighting pitch is defined as an axial distance covered by a complete turn of the helical flighting.

In a further embodiment according to the invention the helical flighting pitch increases with the axial distance measured from the orifice. As a result, an axially oriented pressure gradient can be exerted by the auger on the reservoir's content contained within the volume established by a revolution of the auger. Preferably, the helical flighting pitch monotonically increases with the distance from the orifice.

In a further embodiment according to the invention the device comprises a measuring apparatus for measuring a quantity of the reservoir's content conveyed through the orifice. Based on a measurement acquired by way of the measuring apparatus, the actuator arrangement can be controlled. As a result, a more accurate dosing of powder like medication to an environment is obtained.

In an embodiment according to the invention the measuring apparatus comprises a revolution counter for counting a number of revolutions made by the auger. Assuming that the helical flighting height and the helical flighting pitch are both known, the number of revolutions made by the auger provides an accurate measurement for the amount of the reservoir's content conveyed through the orifice.

The capsule according to the invention is defined in claim 13. The capsule can be made of any suitable material, such as a biocompatible plastic. Apart from being non-reactive to a medication or an acid, a biocompatible plastic material has a density which is larger than water which will ensure the capsule neither to float above water nor to be detained inside a gastrointestinal tract.

The invention is highly suitable for application in the field of targeted and precisely controlled delivery of a medication, especially a powder like medication, to an environment, particularly a humid environment, which environment may be inside a human or an animal body. A likely environment is a gastrointestinal tract.

BRIEF DESCRIPTION OF THE DRAWINGS

The invention and its advantages are further elucidated by way of example with reference to the drawings in which.

DETAILED DESCRIPTION OF THE EMBODIMENTS

Figure 1:
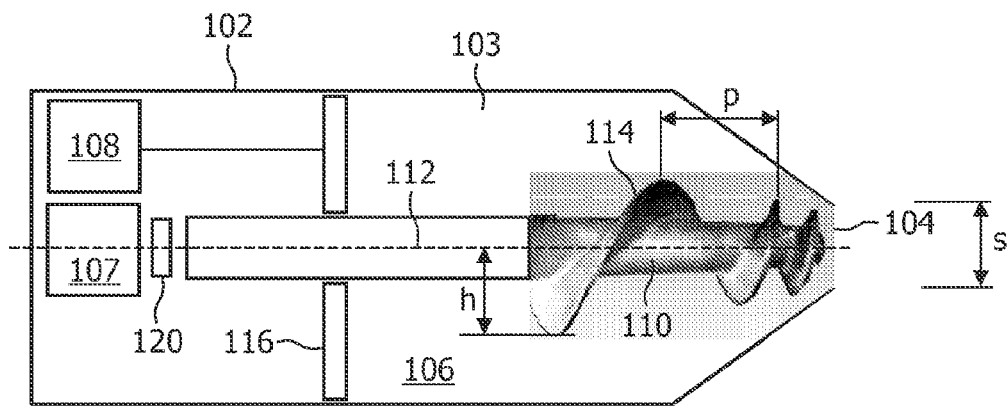
FIG. 1 schematically displays an embodiment of the device according to the invention, wherein a piston is driveable by an actuator arrangement.
Figure 2:
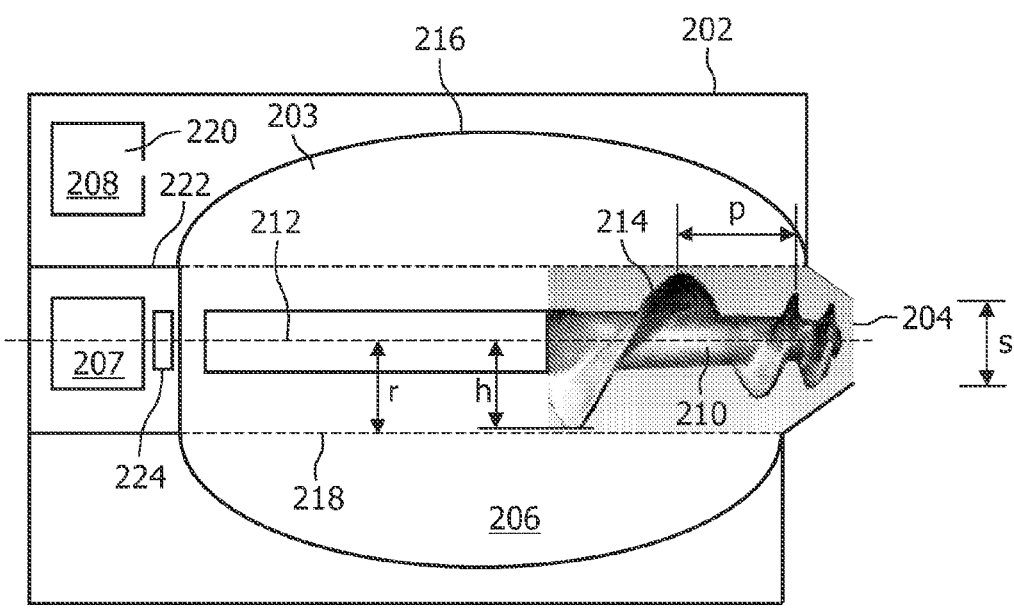
FIG. 2 schematically shows an embodiment of the device according to the invention, wherein a collapsible barrier is arranged for pressurizing a reservoir's content.
Figure 3:
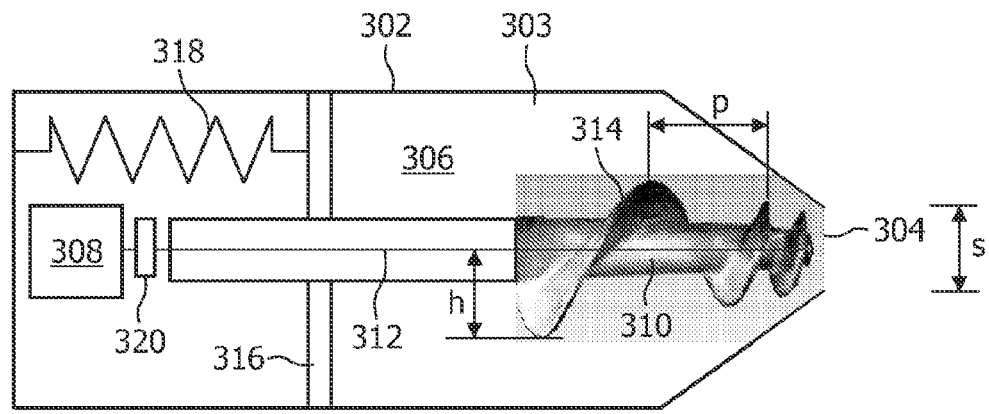
FIG. 3 schematically depicts an embodiment of the device according to the invention, in which a piston is arranged for pressurizing a reservoir's content, wherein a spring facility serves for pretensioning the piston.

FIG. 1 displays a preferred embodiment according to the invention in the form of a capsule 102 comprising a reservoir 103. The capsule 102 is at made of a biocompatible plastic, such as a medical grade polyethylene. The reservoir 103 is provided with an orifice 104. The orifice 104 can be provided with a hydrophobic coating as to minimize a diffusion into the reservoir 103 of a humidity present in a moist environment surrounding the capsule 102. The reservoir 103 contains a reservoir's content 106 which is a powder like medication. An actuator arrangement comprises an actuator 107 and a further actuator 108. The actuator 107, which is a spring actuator, an electromagnetic actuator, a hydraulic actuator or a piezoelectric actuator, causes an auger 110 to rotate around an axis of revolution 112 during use. The auger 110 is made of a biocompatible plastic or a stainless steel and extends into the reservoir 103 in order to provide a mechanical interaction with the reservoir's content 106 with the purpose of both conveying the reservoir's content 106 to the orifice 104 and annulling a solidification of the reservoir's content 106. The solidification of the reservoir's content 106 is caused by way of a humidification in the moist environment surrounding the capsule 102 or by way of a humidity already contained in the reservoir's content 106. The solidification of the reservoir's content 106 is annulled by way of pulverization through a revolution of the auger 110 during use. The auger 110 is provided with a helical flighting 114. The helical flighting has a helical flighting height h which monotonically increases with an axial distance from the orifice 104. Proximal to the orifice 104, the helical flighting height h matches a size s of the orifice with the purpose of continuation of the auger 110 up to and including the orifice 104. In addition to that, the helical flighting 114 has a helical flighting pitch p which monotonically increases with an axial distance measured from the orifice 104. As a result an axially oriented pressure gradient can be exerted on the reservoir's content 106 contained within a volume, which volume is established by a revolution of the auger 110. A piston 116 serves for pressurizing the reservoir's content 106. With that, under a pressure provided by the piston 116 during use, the reservoir's content 106 is continuously fed into the helical flighting 114 of the auger 110. The piston 116, which is made of a biocompatible plastic or a stainless steel and is optionally provided with a non-sticky coating, is driveable by the further actuator 108. The further actuator 108 is an electromagnetic actuator or a hydraulic actuator. A measurement apparatus 120, comprising a revolution counter, serves for measuring a number of revolutions made by the auger 110. A measurement signal generated by the measurement apparatus 120 serves for controlling the actuator 107 and the further actuator 108. Since the helical flighting height h and the helical flighting pitch p are both known, the number of revolutions made by the auger 110 provides a measurement for the amount of the reservoir's content 106 conveyed through the orifice 104. For the purpose of a high auger transportation efficiency, an inside surface of the reservoir 103 can be provided with a non-sticky coating whereas the helical flighting 114 of the auger 110 can be provided with certain roughness features.

FIG. 2 displays an embodiment according to the invention in the form of a capsule 202 comprising a reservoir 203. The capsule 202 is made of a biocompatible plastic. The reservoir 203 is provided with an orifice 204. The reservoir 203 contains a reservoir's content 206 which is a powder like medication. An actuator arrangement 207 comprises an actuator 207 and a further actuator 208. The actuator 207, which is a spring actuator, an electromagnetic actuator, a hydraulic actuator or a piezoelectric actuator, causes an auger 210 to revolute during use around an axis of revolution 212. The auger 210 is provided in the reservoir 203 in order to provide mechanical interaction with the reservoir's content 206 with the purpose of both conveying the reservoir's content 206 to the orifice 204 and annulling a solidification of the reservoir's content 206. The auger 210 is provided with a helical flighting 214. The helical flighting has a helical flighting height h which monotonically increases with an axial distance from the orifice 204. Proximal to the orifice 204, the helical flighting height h matches a size s of the orifice with the purpose of continuation of the auger 210 up to and including the orifice 204. In addition to that, the helical flighting 214 has a helical flighting pitch p which monotonically increases with an axial distance from the orifice 204. A collapsible barrier 216 for pressurizing the reservoir's content 206 is contained in the reservoir 203. With that, under the pressure provided by the collapsible barrier 216, the reservoir's content 206 is continuously fed into the helical flighting 214 of the auger 210. The collapsible barrier 216 is conformable to a tube like grid 218 installed around the auger 210 which tube like grid 218 is to prevent the collapsible barrier 216 from contacting the auger 210. By choosing a radius r of the grid 218 minimally, i.e. by choosing it only slightly larger than the maximum level of the helical flighting height h, a residue of the reservoir's content 206 is minimized. The collapsible barrier 216 is compressible by the further actuator 208. The further actuator 208 comprises a cartridge 220 that releases an inert gas upon actuation in the volume established by the reservoir 203, the collapsible barrier 216 and a seal 222 as to provide a pressure to the collapsible barrier 216. A measurement apparatus 224 comprising a revolution counter, serves for measuring a number of revolutions made by the auger 210. A measurement signal generated by the measurement apparatus 224 serves for controlling the actuator 207 and the further actuator 208.

FIG. 3 displays an embodiment according to the invention in the form of a capsule 302 comprising a reservoir 303. The reservoir is provided with an orifice 304. The reservoir 303 contains a reservoir's content 306 which is a powder like medication. An actuator arrangement comprises an actuator 308. The actuator 308 causes an auger 310 to revolute around an axis of revolution 312 during use. The auger 310 is present in the reservoir 303 in order to provide a mechanical interaction with the reservoir's content 306 with the purpose of both conveying the reservoir's content 306 to the orifice 304 and annulling a solidification of the reservoir's content 306. The auger 310 is provided with a helical flighting 314. The helical flighting has a helical flighting height h which increases with an axial distance from the orifice 304. Proximal to the orifice 304, the helical flighting height h matches a size s of the orifice with the purpose of continuation of the auger 310 up to and including the orifice 304. In addition to that, the helical flighting 314 has a helical flighting pitch p which increases with an axial distance from the orifice 304. As a result an axially oriented pressure gradient can be exerted on the reservoir's content 306 contained within a volume which volume is established by a revolution of the auger 310. A piston 316 serves for pressurizing the reservoir's content 306. With that, under a pressure provided by the piston 316 during use, the reservoir's content 306 is continuously fed into the helical flighting 314 of the auger 310. The piston 316 is pretensioned to the reservoir's content 306 by way a facility for pretensioning. The facility for pretensioning comprises an elastic mechanical spring 318. The facility for pretensioning the piston 316 to the reservoir's content 306 may alternatively comprise an air spring, a repulsive magnetic element or a combination thereof. Trough this, a continuous energizing of an actuator to provide a pressure to the reservoir's content 304 is prevented from. A measurement apparatus 320 comprising a revolution counter, serves for measuring a number of revolutions made by the auger 310. A measurement signal generated by the measurement apparatus 320 serves for controlling the actuator 308.

Figure 4:
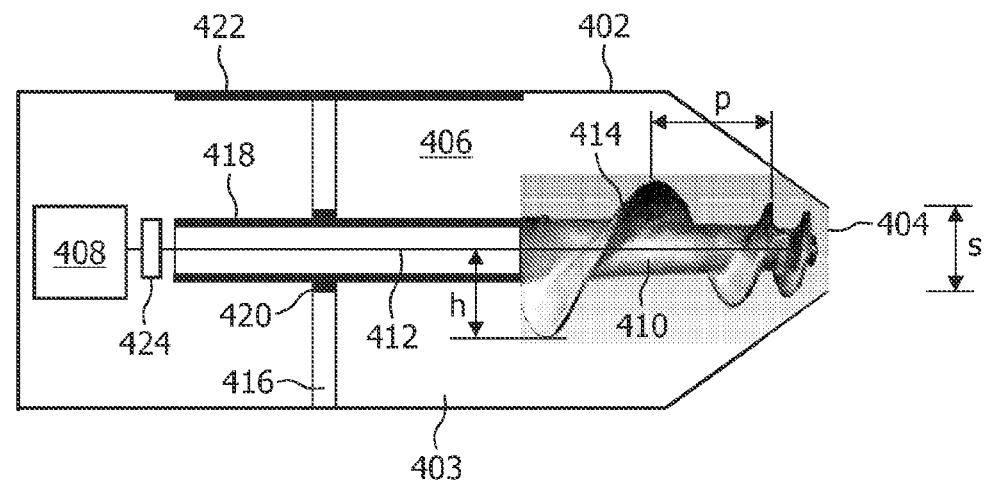
FIG. 4 schematically shows an embodiment of the device according to the invention, wherein a piston is driveable by an auger.

FIG. 4 displays an embodiment according to the invention in the form of a capsule 402 comprising a reservoir 403. The reservoir is provided with an orifice 404. The orifice 404 can be provided with a hydrophobic coating as to minimize a diffusion into the reservoir 403 of a humidity present in a moist environment surrounding the capsule 402. The reservoir 403 contains a reservoir's content 406 which is a powder like medication. An actuator arrangement comprises an actuator 408. The actuator 408, which is a spring actuator, an electromagnetic actuator, a hydraulic actuator or a piezoelectric actuator, causes an auger 410 to rotate around an axis of revolution 412 during use. The auger 410 extends into the reservoir 403 with the purpose of providing a mechanical interaction with the reservoir's content 406. The auger 410 is provided with a helical flighting 414. The helical flighting has a helical flighting height h which increases with an axial distance from the orifice 404. Proximal to the orifice 404, the helical flighting height h matches a size s of the orifice with the purpose of continuation of the auger 110 up to and including the orifice 404. In addition to that, the helical flighting 414 has a helical flighting pitch p which increases with an axial distance from the orifice 404. A piston 416 serves for pressurizing the reservoir's content 406. The piston 416 for pressurizing the reservoir's content 406 is driveable by the auger 410. For driving the piston 416, the auger 410 is supplied with an auger screw thread 418 for cooperation with a piston screw thread 420. A rail 422 is supplied to the reservoir 402 to accurately guide a displacement of the piston 416 and to prevent the piston 416 from rotating with the auger 410. A measurement apparatus 424 comprising a revolution counter is arranged for measuring a number of revolutions made by the auger 410. A measurement signal generated by the measurement apparatus 424 serves for controlling the actuator 408.

Figure 5:
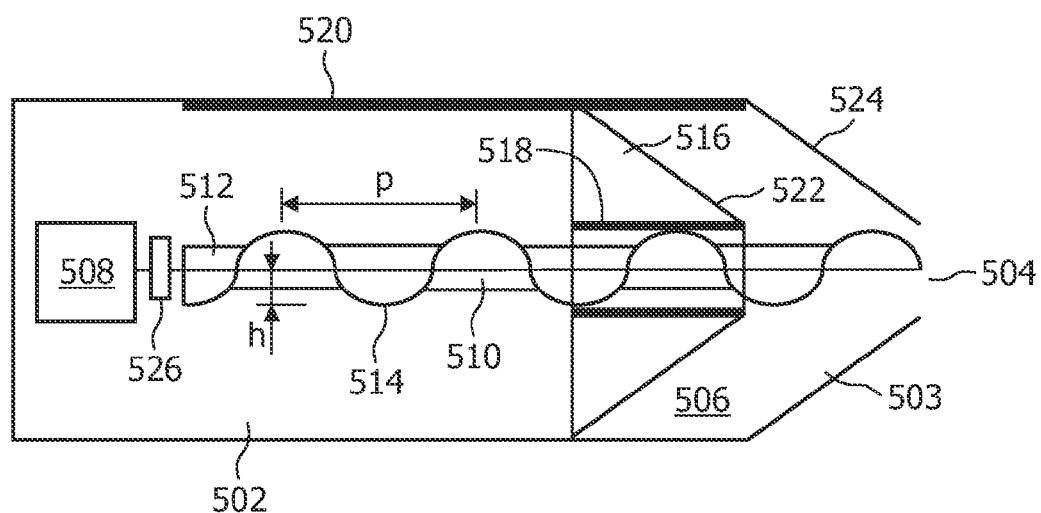
FIG. 5 schematically displays an embodiment of the device according to the invention, wherein a piston's surface profile matches a reservoir's surface profile surrounding an orifice.

FIG. 5 displays an embodiment according to the invention in the form of a capsule 502 comprising a reservoir 503. The reservoir 503 is provided with an orifice 504. The reservoir 503 contains a reservoir's content 506 which is a powder like medication. An actuator arrangement comprises an actuator 508. The actuator 508 causes an auger 510 to revolute around an axis of revolution 512 during use. The auger 510 extends in the reservoir 503 in order to provide a mechanical interaction with the reservoir's content 506 with the purpose of both conveying the reservoir's content 506 to the orifice 504 and annulling a solidification of the reservoir's content 506. The auger 510 is provided with a helical flighting 514. A piston 516 for pressurizing the reservoir's content 506 is driveable by the auger 510. With that, under a pressure provided by the piston 516 during use, the reservoir's content 506 are continuously fed into the helical flighting 514 of the auger 510. For driving the piston 516, the auger 510 is supplied with a constant helical flighting height h and a constant helical flighting pitch p. The helical flighting 514 is in cooperation with a piston screw thread 518. A rail 520 is supplied to the reservoir 502 to accurately guide a displacement of the piston 516 and to prevent the piston 516 from rotating with the auger 510. By driving the piston 516 through the auger 510, the prerequisite for a further actuator to drive the piston 516 is circumvented. The piston 516 has a surface profile 522 that corresponds to a reservoir's surface profile 524 adjacent to the orifice 504. Consequently, the piston 516 is transportable as far as the reservoir's orifice 504. As a result, a residue of the reservoir's content 506 is minimized. A measurement apparatus 526 comprising a revolution counter is arranged counting a number of revolutions made by the auger 510. A measurement signal generated by the measurement apparatus 526 is serving for controlling the actuator 508.

While the invention has been illustrated and described in detail in the drawings and in the foregoing description, the illustrations and the description are to be considered illustrative or exemplary and not restrictive. The invention is not limited to the disclosed embodiments. It is noted that the apparatus according to the invention and all its components can be made by applying processes and materials known per se. In the set of claims and the description the word "comprising" does not exclude other elements and the indefinite article "a" or "an" does not exclude a plurality. Any reference signs in the claims should not be construed as limiting the scope. It is further noted that all possible combinations of features as defined in the set of claims are part of the invention.

The invention claimed is:

1. A device comprising:
   a capsule adapted for placement into a patient's gastrointestinal tract;
   a reservoir in the capsule having an orifice;
   an auger rotatable about an axis and disposed at least partially in the reservoir for conveying contents of the reservoir through the orifice;
   a pressurizing member configured to pressurize the contents of the reservoir and that is movable relative to the auger;
   a first actuator configured to provide a force along the axis on the member; and
   a second actuator configured to rotate the auger.

2. The device according to claim 1, wherein the member is a piston.

3. The device according to claim 1, wherein the auger has an axially varying helical flighting height.

4. The device according to claim 3, wherein the axially varying helical flighting height increases with an axial distance from the orifice.

5. The device according to claim 1, wherein the auger has an axially varying helical flighting pitch.

6. The device according to claim 4, wherein the axially varying helical flighting pitch monotonically increases with an axial distance from the orifice.

7. The device according to claim 1, comprising a measuring apparatus for measuring a quantity of the reservoir's content conveyed through the orifice.

8. The device according to claim 7, wherein the measuring apparatus comprises a revolution counter for counting a number of revolutions made by the auger.

9. A method of treating a patient comprising:
  administering the device of claim 1 by causing the patient to swallow the device; and
  while the device is in the gastrointestinal tract, controlling the second actuator to cause the auger to rotate, thereby releasing the contents of the reservoir to be released through the orifice.

10. A device comprising:
  an elongate capsule configured for insertion into a bodily opening, the capsule having a longitudinal axis and an opening at a longitudinal end of the capsule;
  a reservoir disposed in the capsule and configured to hold a substance, the reservoir being in fluid communication with the opening;
  an auger disposed completely in the capsule and at least partially disposed in the reservoir in the capsule, the auger being arranged to rotate about the longitudinal axis of the capsule;
  a first actuator completely disposed in the capsule and configured to rotate the auger;
  a pressurizing member disposed in the capsule and configured to apply a pressure on the reservoir; and
  a second actuator completely disposed in the capsule and configured to apply a force on the member at least partially along a direction of the longitudinal axis of the capsule.

11. The device of claim 10, wherein the pressurizing member comprises a piston.

12. The device according to claim 1, wherein the pressurizing member is a piston and further comprising a facility for pretensioning the piston to the contents of the reservoir.

13. The device according to claim 12, wherein the piston is driveable by the auger.

14. The device according to claim 12, wherein a surface profile of the piston matches a surface profile of a surface of the reservoir adjacent the orifice.

15. The device according to claim 1, wherein the pressurizing member is a piston and the piston is driveable by the auger.

16. The device according to claim 15, wherein a surface profile of the piston matches a surface profile of a surface of the reservoir adjacent the orifice.

17. The device according to claim 1, wherein the pressurizing member is a piston and a surface profile of the piston matches a surface profile of a surface of the reservoir adjacent the orifice.

18. The device according to claim 1, wherein the pressurizing member comprises a collapsible barrier.

19. The device of claim 10, wherein the pressurizing member comprises a collapsible barrier.

* * * * *